(12) United States Patent
Matzger et al.

(10) Patent No.: US 9,393,548 B2
(45) Date of Patent: Jul. 19, 2016

(54) RAPID AND ENHANCED ACTIVATION OF MICROPOROUS COORDINATION POLYMERS BY FLOWING SUPERCRITICAL $CO_2$

(71) Applicant: The Regents of the University of Michigan, Ann Arbor, MI (US)

(72) Inventors: Adam J. Matzger, Ann Arbor, MI (US); Baojian Liu, Hangzhou (CN); Antek G. Wong-Foy, Ann Arbor, MI (US)

(73) Assignee: The Regents Of The University Of Michigan, Ann Arbor, MI (US)

( * ) Notice: Subject to any disclaimer, the term of this patent is extended or adjusted under 35 U.S.C. 154(b) by 174 days.

(21) Appl. No.: 14/139,184

(22) Filed: Dec. 23, 2013

(65) Prior Publication Data

US 2014/0179514 A1    Jun. 26, 2014

Related U.S. Application Data (60) Provisional application No. 61/745,950, filed on Dec. 26, 2012.

(51) Int. Cl.
| | |
|---|---|
| *B01J 20/30* | (2006.01) |
| *B01J 20/28* | (2006.01) |
| *B01J 31/16* | (2006.01) |
| *C07C 51/41* | (2006.01) |
| *C07F 1/08* | (2006.01) |
| *C07F 3/06* | (2006.01) |
| *C07F 7/00* | (2006.01) |
| *B01J 20/22* | (2006.01) |

(52) U.S. Cl.
CPC ............ *B01J 20/3085* (2013.01); *B01J 20/226* (2013.01); *B01J 20/28054* (2013.01); *B01J 20/28066* (2013.01); *B01J 31/1691* (2013.01); *C07C 51/418* (2013.01); *C07F 1/08* (2013.01); *C07F 3/06* (2013.01); *C07F 7/006* (2013.01); *Y02P 20/544* (2015.11)

(58) Field of Classification Search
CPC .............. B01J 20/226; B01J 20/28054; B01J 20/28066; B01J 20/3085; B01J 31/1691; C07C 51/418; C07F 1/08; C07F 3/06; C07F 7/006

See application file for complete search history.

(56) References Cited

U.S. PATENT DOCUMENTS

2011/0144367 A1* 6/2011 Hupp et al. ................... 556/121

FOREIGN PATENT DOCUMENTS

KR    20100125771    * 1/2010

OTHER PUBLICATIONS

Translation of KR20100125771, Jan. 12, 2010, p. 1-12.*
Pazuki, et al., "Correlation and Prediction of the Solubility of CO2 in a Mixture of Organic Solution SOlvents," Theoretical Foundations of Chemical Engineering, vol. 39, No. 3, 2005, pp. 240-245.*
Li et al, "Top-down fabrication of crystalline metal-organic framework nanosheets," Chem. Commun., 2011, 47, 8436-8438.*
Park et al., "Stepwise and hysteretic sorption of N2, O2, CO2 and H2 gases in a porous metal-organic framework [Zn2(BPnDC)2(bpy)]," Chem. Commun., 2010, 46, 610-612.*

* cited by examiner

*Primary Examiner* — Paul A Zucker
*Assistant Examiner* — Mark Luderer
(74) *Attorney, Agent, or Firm* — Harness, Dickey & Pierce, PLC (57) ABSTRACT

Flowing supercritical $CO_2$ is used to activate metal organic framework materials (MOF). MOFs are activated directly from N,N-dimethylformamide (DMF) thus avoiding exchange with a volatile solvent. Most MCPs display increased surface areas directly after treatment although those with coordinatively unsaturated metal centers benefit from additional heating.

20 Claims, 2 Drawing Sheets

RAPID AND ENHANCED ACTIVATION OF MICROPOROUS COORDINATION POLYMERS BY FLOWING SUPERCRITICAL CO₂

CROSS REFERENCE TO EARLIER APPLICATIONS

This application claims the benefit of U.S. provisional application Ser. No. 61/745,950 filed Dec. 26, 2012, the entire disclosure of which is incorporated by reference.

GOVERNMENT SUPPORT

This invention was made with government support under DE-SC0004888 awarded by the Department of Energy. The Government has certain rights in the invention.

BACKGROUND

Microporous coordination polymers (MCPs) are poised to make a commercial impact on sorption technologies. Uniquely high performance has been demonstrated for gas storage,[1] separations,[2] $CO_2$ capture,[3] and catalysis.[4] When considering that widely available activated carbons and zeolites can come close to reaching these performance levels at a cost of dollars per pound of sorbent and are already broadly deployed, the difficulty associated with deploying MCPs as drop in replacements for these established sorbents becomes obvious.

Advancing the promise of MCPs into impact is hampered by a number of synthetic issues and complexities associated with material activation. The majority of ligands employed thus far are impractical from a cost standpoint. Significant advances have been made by leveraging inexpensive starting materials through mixed linker MCPs[5] and complexity generating schemes such as post synthetic modification.[6] These new methods have the potential to control starting material costs sufficiently to make industrial synthesis possible; however, the material activation regimen remains problematic.

Often the solvent of synthesis is exchanged multiple times over several days and with multiple solvent types to facilitate guest removal and evacuation. In some cases this process must include supercritical $CO_2$ (SC—$CO_2$) drying in order to maintain porosity. Therefore even controlling the cost of material synthesis is insufficient without a means of economically activating the sorbent.

Some MCPs are unstable upon guest removal and undergo pore collapse. Hupp and co-workers proposed that high surface areas and permanent porosity for this kind of MCP could be obtained through activation by SC—$CO_2$.[7a] Summarizing the general procedure for batch SC—$CO_2$ activation as typically practiced,[7a] as-synthesized crystals are washed with N,N-dimethylformamide (DMF) and then exchanged with solvents such as acetone,[5b] absolute ethanol,[7a-f] or chloroform followed by hexane.[7g] After solvent exchange, the solvated crystals are transferred into a critical point dryer and treated through several cycles of soaking in liquid $CO_2$ and venting. After the solvent is exchanged by liquid $CO_2$, the temperature is raised to 40° C. and the pressure to 80-200 bar followed by several hours of treatment at supercritical conditions. Release of the supercritical conditions and gradual venting of the $CO_2$ yields the activated sample.

SUMMARY

Here we describe the broad utility of flowing SC—$CO_2$ deployed in a bed configuration for the production of high performance MCPs. This method contrasts with the current practice in being more rapid and continuous in the guest extraction process. A wide variety of MCPs is examined here with activation by flowing SC—$CO_2$ conditions, with or without solvent exchange to replace the solvent of sunthesis.

The MCP's are selected from metal organic framework materials (MOF) prepared from reacting a source of metal cation (or mixture of metal cations) with an organic linker (or mixture of linkers) such as those selected from compounds with a plurality of carboxyl groups. Crystals isolated from the reaction mixture contain occluded solvent of synthesis; an optional after solvent exchange, the occluded solvent is the exchange solvent. Activation of the MOF materials involves removing the occluded solvent whatever the source, which is normally accompanied by a significant increase in the surface area of the porous MOF.

A method of making a porous material involves a) combining a metal salt and an organic linker in a solvent or solvents in which both are soluble, b) exposing the combined metal salt and organic linker to conditions under which they react to form a porous material comprising a metal-organic framework, c) obtaining crystals of the porous material from the reaction mixture, wherein the crystals comprise the metal-organic framework material and occluded solvent of reaction, and then d) exposing the crystals to flowing supercritical carbon dioxide to remove occluded solvent from the crystals and provide an activated material. The method includes an optional step of exchanging the solvent of reaction for another solvent to achieve other advantages. That said, an advantage of the method is that a solvent exchange step is not strictly required, and the flowing SC—$CO_2$ conditions are capable of removing solvents lacking high solubility in SC—$CO_2$, such as those like N,N-dimethylformamide (DMF) and N,N-diethylformamide (DEF) commonly used in synthesis of the porous MOF materials. In various embodiments, the method is an improvement over the use of static liquid and supercritical $CO_2$ for washing the solvent-containing crystals in a batch-type reaction.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DESCRIPTION

For convenient reference throughout, the abbreviations SC—$CO_2$, sc-$CO_2$, SC—$CO_2$, and sc-$CO_2$ are used interchangeably herein for supercritical carbon dioxide. Reaction solvent, solvent of synthesis and similar phrases are likewise used interchangeably, except where the context provides otherwise.

In one embodiment a method for the treatment of a solvent containing metal organic framework material (MOF) is provided to increase its internal surface area or porosity. The method involves introducing carbon dioxide into a vessel containing the solvent containing MOF, and venting the carbon dioxide ($CO_2$) from the vessel while maintaining supercritical conditions for carbon dioxide in the vessel. In this way, the solvent-containing MOF is exposed to flowing supercritical carbon dioxide conditions to dry the material and produce an activated MOF.

In another embodiment, a method of making a porous material is provided. The method includes, a) combining the metal salt and an organic linker in a reaction solvents or solvents in which both are soluble, b) exposing the combined metal salts and organic linker to conditions under which they react to form a porous material comprising a metal organic framework, c) obtaining crystals of the porous material from the reaction mixture of the preceding step, wherein the crystals comprise the metal organic framework material and occluded solvent of reaction, and d) exposing the crystals to flowing supercritical carbon dioxide to remove occluded solvent from the crystals and provide an activated material.

In another method of making and activating a porous material comprising a metal organic framework, the steps include first reacting a metal cation selected from $Zn^{2+}$, $cu^{2+}$, $Mg^{2+}$, $Ni^{2+}$, $Co^{2+}$, and $Mn^{2+}$ with an organic linker composition to form an MOF material having occluded solvent of synthesis. Thereafter, the MOF material with occluded solvent of synthesis is optionally exposed to a second solvent to exchange out the solvent of synthesis. Then, the MOF material is dried by exposing the MOF material that contains either the solvent of synthesis or the second solvent to conditions of flowing supercritical carbon dioxide to make the activated porous material.

In one aspect, the methods involve an improvement over a prior art method of using supercritical carbon dioxide. In the method of preparing a metal organic framework material by reacting a metal salt land an organic linker in a solvent synthesis, recovering crystals of the MOF material, optionally exchanging the solvent of synthesis and a second solvent miscible with supercritical carbon dioxide, and exposing the crystals to liquid carbon dioxide and then to supercritical dioxide to remove the miscible solvent, the improvement provides exposing the crystals to flowing supercritical carbon dioxide to remove the solvent.

The methods described herein optionally include an additional step of heating the MOF material after it has been dried by being subject to flowing supercritical carbon dioxide conditions, where the heating is optionally and preferably under vacuum to further remove solvent and activate the material.

In another modification of the methods described herein, instead of flowing supercritical carbon dioxide, the solvent containing MOF is exposed to flowing liquid carbon dioxide to remove solvent and activate the material. In a non-limiting example, carbon dioxide is introduced into a vessel containing the solvent containing MOF, the temperature and pressure conditions are adjusted to obtain liquid carbon dioxide, and carbon dioxide is then vented from the vessel while maintaining the conditions for liquid carbon dioxide in the vessel. In other modifications of the methods described herein, the solvent-containing MOF is subject to conditions of both of flowing liquid carbon dioxide and of flowing supercritical carbon dioxide. In the methods described herein, there is normally a further step of releasing the supercritical carbon dioxide or liquid carbon dioxide conditions, usually by relieving the pressure, and venting off the resulting gaseous carbon dioxide from the vessel to recover the dried MOF materials.

In the methods described herein, the solvent of a synthesis is selected from solvents in which both of the starting materials are soluble, both N,N-dimethylformamide (DMF) and N,N-diethylformamide (DEF) have been found to be useful reaction solvents, especially when the linkers, further described below, are made of molecules having a plurality of carboxyl groups. Both DMF and DEF are not miscible in carbon dioxide. As a result, methods of the prior art have tended to require the non-miscible solvent of reaction be exchanged out with another solvent that is more soluble or even miscible in carbon dioxide or supercritical carbon dioxide. Before the flowing supercritical carbon dioxide conditions of the present teachings were developed, an extra step of solvent exchange was normally required in order to activate the materials. Suitable miscible solvents that could be exchanged with DMF or DEF of synthesis include hexane, chloroform, methylene chloride, tetrahydrofuran, methanol, ethanol, and acetone, to give non-limiting examples. A solvent exchange can be carried out on MOF materials containing occluded solvents of synthesis before drying the material with the flowing supercritical carbon dioxide conditions described herein.

In certain embodiments, such as when the MOF materials are synthesized without using solvent, the invention provides for activation of the as-synthesized materials by subjecting them to flowing sc-CO2 or flowing liquid oxygen, where the flowing conditions do not lead to removal of solvent. Such a solventless activation is provided by the flowing conditions described herein. In these embodiments, the material to be dried is an MOF material that does not have occluded solvent. In these embodiments, a MOF material is activated by subjecting it to conditions of flowing sc-CO2 or of flowing liquid oxygen as described herein.

In various embodiments, the porous material such as an MOF is made by reacting a source of a metal with an organic linker and a solvent in which both are soluble. In a non-limiting example, the organic linker and the metal source—a metal salt, carbonate or oxide, in non-limiting fashion—are partially or fully dissolved in an appropriate solvent and reacted. The reaction can occur in a closed vessel at elevated temperature or by subjecting the solution to microwaves, ultrasound, or electrochemical treatments. MOF materials can also be prepared by milling solid-phase metal derivatives and solid phase organic linkers in the presence of a liquid. As a result of the synthesis in the presence of the solvents, the resulting MOF material prepared from the reaction mixture includes at least some occluded solvent, which is to be removed in a series of post-synthesis steps described herein. The product of synthesis, which is normally a crystalline MOF material, is isolated from the reaction mixture by precipitation, filtration, and other conventional means and subjected to other steps to activate the material. In a first step, it is possible to subject the crystals obtained from the reaction mixture to solvent exchange which, as noted above, can be used to replace occluded solvent of synthesis with a solvent that is more soluble in carbon dioxide, or even miscible in carbon dioxide. In the prior art, this step was needed in order for the extraction with statically applied supercritical carbon dioxide to function. Solvent exchange is accomplished in conventional matter by soaking the crystals containing occluded solvent in other solvents optionally exchanging the crystals one or more times during the hours long or day long soakings. The result of the solvent exchange is a crystalline MOF material having occluded exchange solvent.

In the methods disclosed herein, the source of solvent with the initial reaction to form the MOF material is selected from suitable soluble sources, including salts such as nitrates, carbonates, oxides, acetates, and the like. The identity of the metal is not necessarily limited. In various embodiments, the source of metal includes a metal cat ion selected from $Zn^{2+}$, $Cu^{2+}$, $Mg^{2+}$, $Ni^{2+}$, $Co^{2+}$, and $Ni^{2+}$. Zinc nitrate and copper (II) nitrate are common starting materials. Commercially available hydrates can be used.

In methods described herein, the source of metal is reacted with an organic linker composition in a solvent system to form an MOF material. The organic linker composition contains one or more organic compounds that serve as linkers in the MOF material. In one embodiment, the linker compositions contain one or more organic compounds that contain two or more carboxyl groups. In various embodiments, the linker contains two or more carboxyl groups that are attached to an aromatic ring of the linker. In other embodiments, the linker contains two or more nitrogen containing aromatic rings. In other embodiments, the linker is a compound that contains two or more imidazole rings, or two or more nitrogen heterocycles such as imidazole, tetrazole, and pyridine, or two or more nitrogen containing heterocycles. The following table provides additional examples of suitable linkers, which are commercially available.

TABLE

| Structure | Chemical Name |
| --- | --- |
| | 9,10-Anthracenedicarboxylic acid |
| | Biphenyl-3,3',5,5'-tetracarboxylic acid |
| | Biphenyl-3,4',5-tricarboxylic acid |
| | 2,2'-Diamino-4,4'-stilbenedicarboxylic acid |
| | 5-Cyano-1,3-benzenedicarboxylic acid |

TABLE-continued

| Structure | Chemical Name |
|---|---|
| | 2,5-Diaminoterephthalic acid |
| | 2,5-Dihydroxyterephthalic acid |
| | 2,2'-Dinitro-4,4'-stilbenedicarboxylic acid |
| | 2-Hydroxyterephthalic acid |
| | malonic acid |
| | 2,6-Naphthalenedicarboxylic acid |
| | terephthalic acid |

TABLE-continued

| Structure | Chemical Name |
| --- | --- |
| | [1,1':4',1'']Terphenyl-3,3'',5,5''-tetracarboxylic acid |
| | 3,3',5,5'-Tetracarboxydiphenylmethane |
| | 1,2,4,5-Tetrakis(4-carboxyphenyl)benzene |
| | 4,4',4''-s-Triazine-2,4,6-triyl-tribenzoic acid |
| | trimesic acid, or benzene-1,3,5-tricarboxylic acid |

TABLE-continued

| Structure | Chemical Name |
|---|---|
| | 1,3,5-Tris(4'-carboxy[1,1'-biphenyl]-4-yl)benzene |
| | 1,3,5-Tris(4-carboxyphenyl)benzene |
| | ethanedioic acid |
| | propanedioic acid = malonic acid |
| | butanedioic acid |
| | pentanedioic acid |
| | citric acid |
| | phthalic acid |
| | isophthalic acid |

TABLE-continued

| Structure | Chemical Name |
|---|---|
| | *BTE = 4,4',4''-[benzene-1,3,5-triyl-tris(ethyne-2,1-diyl)]tribenzoate<br>*BPDC = biphenyl-4,4'-dicarboxylate<br>BDC = 1,4-benzenedicarboxylate = terephthalic acid above<br>BTT = benzene-1,3,5-tris(1H-tetrazole)<br>imidazole<br>2-methylimidazole |

There are a wide variety of MOF materials known in the literature. Once series is denoted in the literature as MOF-x, where x is an integer applied more or less in chronological order. For example, MOF-1 through MOF-215 is known. In another series, the MOF materials are designated as IRMOF-y, where y similarly is an integer assigned in chronological order. In general, the MOF-x and the IRMOF-y materials are synthesized from starting metal sources and organic linkers as described herein.

Generally, for a solid to be labeled as a metal organic framework (MOF), it should display the inherent attributes the term implies. These include strong bonding and a geometrically well-defined structure. The MOF materials tend to be characterized by relatively high levels of surface area, making them useful for a variety of applications such as catalysis and gas storage. It has been found that the methods described herein, including the use of flowing supercritical carbon dioxide, can be used to increase the surface area of the MOF materials as they are synthesized. In various embodiments, the methods are particularly useful on porous materials such as MOF's that tend to collapse, since the collapse tends to decrease the surface area of the materials. To mitigate against the collapse of certain materials and to increase the surface area of MOF materials even if they do not exhibit much of a collapse problem, it has been found that subjecting the material to flowing supercritical carbon dioxide helps to remove the solvent and raise the surface area of the material. This process is called activation of the porous materials.

A further advantage is that, by using flowing supercritical carbon dioxide conditions, occluded solvents can be removed from the crystalline MOF materials that are not miscible with carbon dioxide. In various embodiments, this feature allows the crystalline MOF materials to be dried and activated without the lengthy process of solvent exchange which would otherwise be required.

As noted, treatment of MOF materials with the methods described herein involving flowing supercritical carbon dioxide or flowing liquid carbon dioxide tends to increase the internal surface area of the material and to provide increased porosity. Surface area can be measured with conventional means. Examples of surface area measurements and improvements in surface area and porosity upon treatment with flowing supercritical carbon dioxide are given in the examples.

To expose the crystals to flowing supercritical carbon dioxide conditions, it is convenient to place a solvent-containing MOF material in a vessel and to add carbon dioxide to fill the vessel. Upon achieving high enough pressure of carbon dioxide, the carbon dioxide turns into a liquid. Additional carbon dioxide is then added to fill the vessel with liquid carbon dioxide. As noted, in one embodiment, the vessel filled with liquid carbon dioxide can then be vented while maintaining a flowing liquid carbon dioxide.

To obtain supercritical carbon dioxide materials, the temperature is then normally raised above the critical temperature while maintaining the critical pressure of carbon dioxide. Upon imposition of these conditions, the liquid carbon dioxide of the vessel becomes supercritical carbon dioxide. Thereafter, gaseous carbon dioxide continues to be admitted into the vessel while the vessel is maintained at temperature and pressure conditions above the critical point. At the same time, carbon dioxide is vented from the vessel while still maintaining temperature and pressure above the critical points. For convenience, the conditions are maintained in the vessel using a back pressure regulator. Advantages are achieved when the supercritical carbon dioxide flows through the vessel to wash and dry the crystalline MOF materials.

In various embodiments, flowing SC—$CO_2$ conditions are used to activate MCP materials that tend to collapse when activated by conventional solvent evacuation. For flowing SC—$CO_2$ activation, continuous washing of the MCP allows for the removal of less-volatile solvents than is possible by a batch activation method using SC—CO2 washing or conventional evacuation.

Further non-limiting disclosure of the materials and methods is now provided in the following working examples.

EXAMPLES

I. Description of flowing SC—$CO_2$ activation, $N_2$ adsorption, PXRD and TGA

Flowing SC—$CO_2$ Activation. Typically, 50-150 mg solvated crystal slurries were transferred into a 4.6 mm i.d×10 cm stainless steel column using a glass pipette, and then the column was connected to a supercritical $CO_2$ system with a JASCO BP-1580-81 back pressure regulator set at 100 bar. The $CO_2$ was pumped by a JASCO PU-1580-$CO_2$ delivery pump at a flow rate of 2 mL/min and the column was heated at 55° C. through a CERA column heater. After flowing of $CO_2$ for 2.5 h, the flow was stopped and $CO_2$ in the column was gradually released to atmosphere. The activated sample in the column was transferred to a sorption cell in a $N_2$ glove box and the surface area was measured.

$N_2$ Adsorption Measurements. $N_2$ adsorption isotherms were measured by a volumetric method at 77 K in the range $5.00 \times 10^{-3} \leq P/P_0 \leq 1.00$ on a NOVA 4200 (UMCM-9 was measured by Autosorb-1) by Quantachrome Instruments (Boynton Beach, Fla., USA). Ultra-high purity $N_2$ (99.999%) was purchased from Cryogenic Gasses and used as received. Unless otherwise noted, the linear region used for the BET plot was $0.01 \leq P/P_0 \leq 0.1$, and for the Langmuir plot the range was $0.02 \leq P/P_0 \leq 0.3$.

Powder X-ray Diffraction (PXRD) Analysis. Crystals of different MCPs were coated on a Nylon loop using Paratone N mineral oil (Hampton Research) and mounted on a Rigaku R-Axis Spider diffractometer equipped with a Cu Kα X-ray source ($\lambda$=1.5406 Å) operating at 50 kV and 40 mA. Images were collected by transmission with $\chi$=45°, $\phi$ rotating at 10°/min, and $\omega$ oscillating between 80° and 140°. Integration of the images was carried out using the AreaMax (2.0) software package with a step size of 0.02° in 2θ.

Thermogravimetric Analysis (TGA). Measurements of MCP samples activated by different methods were performed on a TA Q50 TGA apparatus. Approximately 1-5 mg of activated sample of different MCPs was loaded into a platinum pan and heating from room temperature to 650° C. at 5 or 10° C./min.

Example 1

A mixed-linker MCP is prepared by reacting zinc nitrate and a equimolar mixture of two linkers, being 2,6-naphthalenedicarboxylic acid and 4,4'-biphenyldicarboxylic acid. Naphthalene-2,6-dicarboxylic acid ($H_2NDC$) (28.7 mg, 0.132 mmol) and biphenyl-4,4'-dicarboxylic acid ($H_2BPDC$) (35.6 mg, 0.147 mmol) were dissolved in a mixture of 6.7 mL of N,N-diethylformamide (DEF) and 13.3 mL of N-methylpyrrolidone (NMP). $Zn(NO_3)_2.6H_2O$ (0.238 g, 0.800 mmol) was added to the solution. The mixture was sonicated for 15 min and heated to 85° C. After 4 days, crystals of a single phase were obtained. After cooling to room temperature the product was isolated by decanting the mother liquor and washed with N,N-dimethylformamide (DMF) (3×10 mL).[S1]

The product, designated as UMCM-9 and represented by the chemical name ($Zn_4O$(naphthalene-2,6-dicarboxylate)$_{1.5}$ (biphenyl-4,4'-dicarboxylate)$_{1.5}$), is activated by SC—$CO_2$ after washing with DMF and exchanging with $CH_2Cl_2$, to yield material with a BET (Brunauer-Emmett-Teller) surface area of 4970 $m^2/g$. When UMCM-9 is directly activated by flowing SC—$CO_2$ from a DMF-solvated sample, the activated sample exhibits an improved BET surface area of 5357 $m^2/g$.

These values, achieved using flowing SC—CO2 conditions, are higher than the 1330 $m^2/g$ achieved from activation by direct evacuation of the $CH_2Cl_2$-exchanged sample.

Example 2

Recently, Han et al.:[7g] reported a highly porous mixed-linker MCP, [$Zn_6$(btb)$_4$(4,4'-bipy)$_3$] (FJI-1, btb=1,3,5-benzenetribenzoate, bipy=4,4'-bipyridyl). A mixture of $Zn(ClO_4)_2.6H_2O$ (0.223 g, 0.6 mmol), 1,3,5-benzenetribenzoic acid ($H_3BTB$) (0.175 g, 0.4 mmol), 4,4'-bipy (0.047 g, 0.3 mmol) and fluoboric acid (48%, 100 μL) in DMF (10 mL) in a 20-mL vial was dissolved by ultrasonic waves 10 minutes and heated at 85° C. for 3 days.[S2] Then the mixture was cooled to room temperature, yielding colorless transparent cubic crystals which were collected and repeatedly washed with DMF three times (3×10 mL). FJI-1 was reported to collapse during evacuation, yet yielded high surface area using the following regimen: 1) as-synthesized FJI-1 crystals were washed with DMF three times, immersed in $CHCl_3$ for 3 days with fresh $CHCl_3$ added every 24 h, and then exchanged with hexane for 3 days with fresh hexane added every 24 h; 2) repeated treatment by injecting and exhausting of SC—$CO_2$ (non-flowing) 12 times over 12 h. This regimen yields a material with a BET surface area of 4043 (Langmuir 4624) $m^2/g$.

Here we followed the same synthesis procedure and the crystals, after washing with DMF, were directly activated using flowing SC—$CO_2$. The BET surface area of FJI-1 is improved to 4813 (Langmuir 5647) $m^2/g$.

Example 3

Encouraged by the above results, four additional MCPs with coordinately saturated metal sites were tested by flowing SC—$CO_2$ activation and compared with the conventional activation by evacuation.

IRMOF-3 was prepared according to slight modification of the published procedure.[53] $Zn(NO_3)_2.6H_2O$ (4.735 g, 15.92 mmol) and 2-aminobenzenedicarboxylic acid (0.96017 g, 5.30 mmol) were dissolved in a 500 mL jar containing 200 mL DMF. The jar was tightly capped and heated in a 100° C. oven for 24 h. After cooling to room temperature, the solution was decanted, then the brown block crystals were washed with DMF three times (3×30 mL). After washing with DMF, some of the crystals were directly activated by flowing SC—$CO_2$. The rest were divided into several parts, transferred to 20 mL vials, exchanged DMF with different solvents ($CH_2Cl_2$, $CHCl_3$, and absolute ethanol) thrice in three days (3×10 mL), then activated by flowing SC—$CO_2$ and conventional evacuation. Conventional activation of IRMOF-3: $CHCl_3$-exchanged sample was evacuated at room temperature for 24 h.

IRMOF-3 has attracted considerable attention because it can be post-synthetically modified covalently via the amine group.[6] Hupp and coworkers[7a] reported that the BET surface area of IRMOF-3 was 2850 $m^2/g$ when activated by SC—$CO_2$ (non-flowing) after solvent exchange with absolute ethanol. IRMOF-3 washed with DMF and then activated by flowing SC—$CO_2$ affords a BET surface area of 3090 $m^2/g$. This result is higher than that obtained by solvent exchange and batch SC—$CO_2$ activation. Additional washing of IRMOF-3 by exchange to absolute ethanol, $CH_2Cl_2$, and $CHCl_3$ does not further improve properties and in fact results in slightly lower surface areas after activation by flowing SC—$CO_2$.

Example 4

MOF-177 and MOF-5 were selected as two additional benchmark MCPs with coordinately saturated metal sites. MOF-177 is a highly porous MCP built from $Zn_4O$ clusters and BTB.[8a]

$Zn(NO_3)_2.6H_2O$ (0.736 g, 2.474 mmol) and $H_3BTB$ (0.360 g, 0.822 mmol) were dissolved in DEF (30 mL) in a 60 mL jar, capped tightly, and heated to 100° C. for 20 h. The solution was decanted, and the clear block crystals were washed with DMF (3×10 mL) and then activated by flowing SC—$CO_2$. Conventional activation method: DMF-solvated crystals were exchanged with $CHCl_3$ thrice in three days (3×10 mL), evacuated to $10^{-3}$ Torr at room temperature for 2 h, heated at a constant rate (1° C./min) to 120° C. for 6 h, then cooled to room temperature.

For the as-synthesized MOF-177 that was washed with DMF three times within 24 h and then activated by flowing SC—$CO_2$; the BET surface area is 4719 (Langmuir 5486) $m^2/g$, which is among the highest ones reported to date.[8b-d] Whereas, MOF-177 of the same batch after exchange with $CHCl_3$ and activation by evacuation gives a lower BET surface area of 4353 (Langmuir 5049) $m^2/g$ MOF-5 (($Zn_4O(BDC)_3$, BDC=1,4-benzene-dicarboxylate)[9a] was synthesized as follows. $Zn(NO_3)_2.6H_2O$ (0.90 g, 3.05 mmol) and 1,4-benzenedicarboxylic acid ($H_2BDC$)

(0.165 g, 1.0 mmol) were dissolved in 25 mL of DEF in a 60 mL jar with a Teflon lined lid. The solution was heated in an oven at 100° C. for 24 h to yield large, cube-shaped crystals.[s5] The jar was then removed from the oven and cooled to room temperature. The crystals were transferred to a 20 mL vial and washed thrice with DMF (3×10 mL) within 24 h, and then activated by flowing SC—$CO_2$. The BET surface area is 3394 (Langmuir 3992) $m^2/g$. This value is among the highest ones reported.[8b,9b]

Example 5

Zinc-based MCPs with coordinately saturated metal sites built from different linkers can be fully activated through flowing SC—$CO_2$ without an extensive solvent exchange process. To demonstrate the broad applicability of this approach, it is necessary to investigate MCPs with other metal clusters. UiO-66 is a zirconium based MCP synthesized from $ZrCl_4$ and $H_2BDC$. UiO-66 was prepared according to published process[s6] with scale-up. $ZrCl_4$ (1.06 g, 4.54 mmol) and $H_2BDC$ (0.68 g, 4.54 mmol) were mixed with 200 mL DMF in a 500 mL jar and sonicated resulting a clear solution. Then the jar was sealed and placed in a pre-heated oven at 120° C. for 24 h. After cooling to room temperature the resulting solid was repeatedly washed with DMF (3×30 mL) and soaked in $CH_2Cl_2$ and absolute ethanol (10 mL) for three days with fresh solvent exchanged every 24 h. Then the samples were activated by flowing SC—$CO_2$.

UiO-66 possesses good stability in water[10a] and has a theoretical surface area of 1021-1084 $m^2/g$.[10b,10c] Flowing SC—$CO_2$ activation of UiO-66 from a DMF-solvated sample affords a BET surface area of 1065 $m^2/g$, which agrees well with theoretical values and is in good accord with the reported highest surface areas achievable by heating above 200° C. under continuous evacuation after solvent exchange with a volatile solvent.[10] If instead UiO-66 is further exchanged from DMF to volatile solvents ($CH_2Cl_2$ or absolute ethanol) followed by flowing SC—$CO_2$ activation, similar surface areas are obtained demonstrating that direct activation is preferable.

Example 6

For MCPs with coordinately unsaturated metal sites, solvents also can act as ligands thus hindering their complete removal by flowing SC—$CO_2$. MOF-74 (Zn/DOBDC, DOBDC=2,5-dioxido-1,4-benzenedicarboxylate) is a good example because it is usually heated at 270° C. under dynamic vacuum after solvent exchange with methanol. Furthermore, the reported BET surface areas are in the range of 750-950 $m^2/g$,[8b,11] which are lower than the isostructural series of M/DOBDC.[11e]

2,5-dioxido-1,4-benzenedicarboxylic acid ($H_4DOBDC$) (1.25 g, 6.51 mmol) and $Zn(NO_3)_2 \cdot 6H_2O$ (5.65 g, 22.0 mmol) were added to a 500 mL jar with 250 mL of DMF and 12.5 mL $H_2O$. The resulting mixture was dissolved by sonication until dissolution of the solids was complete. The jar was tightly sealed with a Teflon-lined cap and placed into an oven heated at 100° C. After 20 h the jar was removed from the oven and the hot mother liquor was decanted and washed with DMF trice (3×30 mL).[s7] Some of the crystals was transferred into a 20 mL vial and replaced DMF with methanol (10 mL). The methanol was replaced 3 times over 6 days. The DMF-solvated and methanol exchanged samples were activated by flowing SC—$CO_2$ and further heated at 270° C. under dynamic vacuum for 14 h.

Figure 1A:
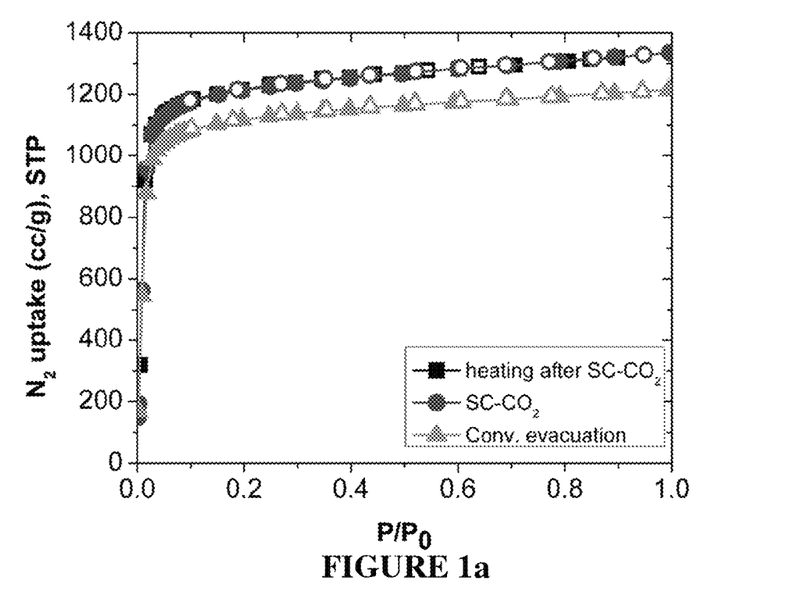
FIG. 1—is a graph which shows a) Nitrogen adsorption (solid) and desorption (open) isotherms at 77 K for MOF-177 activated by flowing SC—$CO_2$ from DMF ●, additional heating at 120° C. for 6 h after SC—$CO_2$ activation ■, and exchange with $CHCl_3$ then evacuation at 120° C. ▲; b) $CO_2$ sorption isotherms on MOF-74 at 298 K, circle: activation by flowing SC—$CO_2$, square: conventional activation.
Figure 1B:
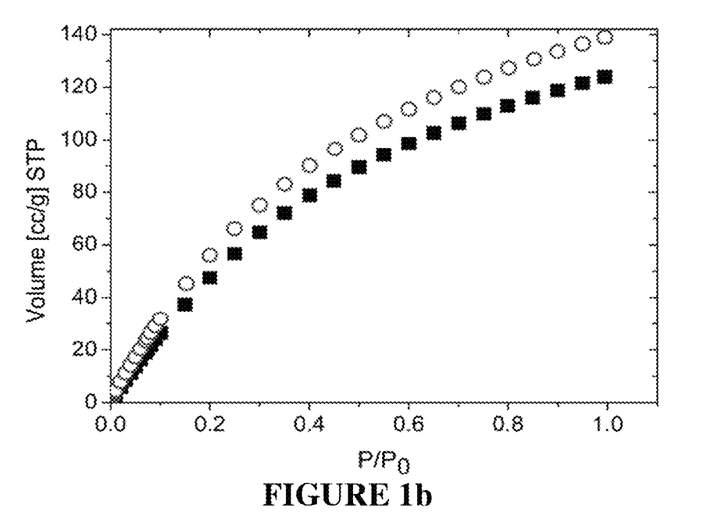

After flowing SC—$CO_2$ drying, the DMF-solvated sample yields a negligible surface area, whereas the methanol exchanged sample affords a low BET surface area of 270 $m^2/g$. The SC—$CO_2$ dried samples were further heated at 270° C. under dynamic vacuum for 14 h, the BET surface areas are 1108 and 1118 $m^2/g$ for DMF- and methanol-exchanged samples respectively. To the best of our knowledge, this surface area is the highest one for MOF-74 to date indicating the efficacy of this method in the context of a very difficult to activate material with coordinately unsaturated metal sites. The flowing SC—$CO_2$ activated sample also exhibits higher $CO_2$ sorption than the conventionally activated one (FIG. 1b), which suggests more efficient exposure of sorption sites.

Example 7

HKUST-1 is an MCP with coordinately unsaturated copper sites and it is challenging to obtain high surface area material. The reported BET surface areas range from 682 to 1944 $m^2/g$.[8b,11a,12] $Cu(NO_3)_2 \cdot 2.5H_2O$ (4.2 g, 18.06 mmol) and 1,3,5-benzenetricarboxylic acid ($H_3BTC$) (2.1 g, 10 mmol) were stirred for 10 minutes in 210 mL of solvent consisting of DMF, ethanol and water (1:1:1) in a 500 mL jar to form a slurry. The tightly capped jar was heated at 85° C. overnight.[s5] After cooling to room temperature, the solution was decanted, then the blue crystals were washed with DMF (3×30 mL). After washing with DMF, some of the crystals were directly activated by flowing SC—$CO_2$. The rest were divided into several parts, transferred to 20 mL vials, exchanged DMF with different solvents ($CH_2Cl_2$, $CHCl_3$, and absolute ethanol) thrice in three days (3×10 mL), then activated by flowing SC—$CO_2$ and conventional evacuation. The SC—$CO_2$ treated samples were further heated under vacuum at 170° C. for 24 h. Conventional activation of HKUST-1: 24 h. $CH_2Cl_2$-exchanged sample was evacuated at room temperature to dry then heated under vacuum at 170° C. for 24 h.

Figure 2:
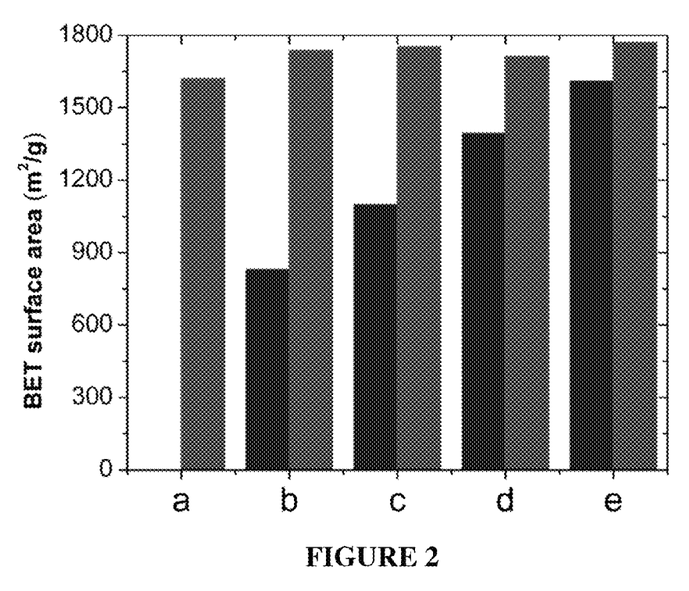
FIG. 2—shows BET surface area of HKUST-1 activated by different methods. a) Conventional heating at 170° C. under vacuum after exchange with $CH_2Cl_2$; flowing SC—$CO_2$ activation (the left of the pair of bar) and additional heating of samples treated with flowing SC—$CO_2$ at 170° C. under vacuum (the right of the pair of bars) from DMF (b), $CH_2Cl_2$ (c), $CHCl_3$ (d), and absolute ethanol (e).

The surface area of samples activated by flowing SC—$CO_2$ from different solvents varies considerably (FIG. 2). Direct flowing SC—$CO_2$ activation from absolute ethanol nearly matches the surface area of material prepared by conventional heating under vacuum. However, additional heating of samples treated with SC—$CO_2$ at 170° C. under vacuum leads to superior surface area in all cases.

Example 8

UMCM-150[13a] is a porous crystalline material containing the common Cu(II) paddlewheel cluster [$Cu_2(O_2CR)_4$], and the rare trinuclear Cu(II) cluster [$Cu_3(O_2CR)_6$].[13b] Biphenyl-3,4',5-tricarboxylic acid (0.060 g, 0.21 mmol) and $Cu(NO_3)_2 \cdot 2.5H_2O$ (0.099 g, 0.042 mmol) were dissolved in DMF/dioxane/$H_2O$ (4:1:1, 30 mL). The solution was placed in a tightly capped 60 mL jar and heated at 75° C. for 12 h. Upon cooling the mother liquor was decanted and replaced thrice with fresh DMF and then activated by flowing SC—$CO_2$. Conventional activation: DMF-solvated crystals were exchanged with fresh acetone three times over a period of three days, the crystals were then activated under vacuum at ambient temperature for 20 h and further evacuated at 100° C. overnight.[s8]

UMCM-150 is a promising adsorbent for liquid fuel desulfurization by selective adsorption of organosulfur compounds.[13c,d] UMCM-150 was originally reported by Wong-Foy et al. with a BET surface area of 2300 $m^2/g^{-1}$ [3a] and then optimized by Park et al. with a BET surface area of 2910 m²/g.[13e] UMCM-150 washed with DMF then activated by flowing SC—$CO_2$ exhibits a BET surface area of 2591 m²/g; additional heating at 100° C. overnight affords a BET surface area of 2873 m²/g.

In summary, the activation of MCPs directly from DMF-solvated crystals by flowing SC—$CO_2$ generally affords higher surface areas than conventional solvent exchange/evacuation or solvent exchange/SC—$CO_2$ treatment. This method is rapid, scalable, energy efficient, and environmentally benign. The results presented in this work have significant implications for rapidly realizing the potential of newly synthesized MCPs and seems especially well suited for streamlining bulk production in industry of highly porous materials of the sort currently unavailable today.

Example 9

Synthesis of UMCM-8

$H_2BDC$ (13.1 mg, 0.0789 mmol) and $H_2NDC$ (17.2 mg, 0.0796 mmol) were dissolved in 6 mL of DEF and the solution was clarified by filtration. $Zn(NO_3)2.6H_2O$ (0.142 g, 0.477 mmol) was added to the solution in a 20 mL vial which was then capped. The mixture was sonicated for 15 min and heated to 85° C. After 3 days, crystals of a single phase were obtained. After cooling to room temperature over the course of 30 min, the product was isolated by decanting the mother liquor and washing with DMF (3×6 mL). The resulting solid was then immersed in 6 mL of $CH_2Cl_2$ for 2 days, during which time the $CH_2Cl_2$ was replaced three times. The solvent was removed under vacuum at room temperature, yielding the porous material. The yield of the reaction, determined from the weight of the solvent-free material (26.4 mg), is 39.6% based on $H_2BDC$. Calculated for $C_{30}H_{15}O_{13}Zn_4$: C, 42.63; H, 1.78. Found: C, 42.65; H, 1.74.

Production of UMCM-8 on a larger scale was conducted as above with $H_2BDC$ (0.460 g, 2.77 mmol), $H_2NDC$ (0.598 g, 2.77 mmol), and $Zn(NO_3)_2.6H_2O$ (4.25 g, 14.28 mmol). The yield of the reaction, determined from the weight of the solvent-free material (1.13 g), is 48.0% based on $H_2BDC$.

Example 10

Synthesis of UMCM-9

$H_2NDC$ (28.7 mg, 0.132 mmol) and $H_2BPDC$ (35.6 mg, 0.147 mmol) were dissolved in a mixture of 6.7 mL of DEF and 13.3 mL of N-methylpyrrolidone. $Zn(NO_3)_2.6H_2O$ (0.238 g, 0.800 mmol) was added to the solution. The mixture was sonicated for 15 min and heated to 85° C. After 4 days, crystals of a single phase were obtained. After cooling to room temperature the product was isolated by decanting the mother liquor and washing with DMF (3×20 mL). The resulting solid was then immersed in 20 mL $CH_2Cl_2$ for 2 days, during which time the $CH_2Cl_2$ was replaced three times. The sample was stored in $CH_2Cl_2$. The yield of the reaction, determined from the weight of the solvent-free material (57.9 mg), is 41.8% based on $H_2NDC$.

Anal. calcd for $C_{39}H_{21}O_{13}Zn_4$: C, 48.82; H, 2.19. Found: C, 47.77; H, 2.05

Example 11

Supercritical $CO_2$ Flow Activation of UMCM-9 and UMCM-8

Activation was performed with a Jasco PU-1580-$CO_2$ delivery pump equipped with a back pressure regulator (Jasco BP-1580-81). The $CH_2Cl_2$-soaked sample from Example 9 or Example 10 (0.1 g) was placed in a metal column and $CH_2Cl_2$ was exchanged with liquid $CO_2$ at 100 bar; the liquid $CO_2$-charged column was heated at 35° C. for 30 min. $CO_2$ was vented over 30 minutes via the back pressure regulator to obtain the activated sample.

Example 12

Synthesis and Successful Activation of IRMOF-8 ($Zn_4O$ (ndc)$_3$, ndc=naphthalene-2,6-dicarboxylate)

Initially, we synthesized IRMOF-8 using common solvothermal routes (hereafter denoted IRMOF-8-HT). After activation by solvent exchange with $CH_2Cl_2$ and subsequent evacuation under reduced pressure (ca. $10^{-2}$ Torr), a BET surface area of 1671 m² g$^{-1}$ was obtained. Materials synthesized in dimethylformamide (DMF) or diethylformamide (DEF), as well as those activated using supercritical $CO^2$, exhibited similar surface areas. Thermogravimetric analysis (TGA) of the activated samples revealed minimal mass loss, suggesting thorough removal of solvent on evacuation (though not discounting occluded non-volatile guests. X-ray diffraction of the material before and after evacuation indicates that bulk crystallinity is maintained; however, reflections in addition to those expected for phase-pure IRMOF-8 are observed. Previous reports have suggested framework interpenetration as the primary cause for low surface area arising from these synthetic procedures. Indeed, comparison with a hypothetical ndc-based framework derived from the structure of IRMOF-912a shows only modest agreement with our experimental data. Although comparison with recently reported interpenetrated Zn/ndc-based systems did not yield better agreement, it stands to reason that the low surface area of IRMOF-8-HT is due, at least in part, to the presence of one or more interpenetrated phases.

Incubation of ndc and $Zn(NO_3)_2.4H_2O$ at room temperature in DEF for one week afforded colorless ca. 100 micron truncated cubic crystals of high optical quality (hereafter denoted IRMOF-8-RT). Data from powder X-ray diffraction showed excellent agreement with that simulated from the original crystal structure. However, upon solvent exchange with $CH_2Cl_2$ and subsequent evacuation, a relatively low BET surface area of 773 m² g$^{-1}$ was obtained. PXRD data of the evacuated material are consistent with partial structural collapse, accounting for a surface area significantly lower than the calculated geometric accessible surface area of 4350 m² g$^{-1}$. Activation using supercritical $CO_2$ applied in a flow apparatus yielded a BET surface area of 4461 m² g$^{-1}$, an unusually high value for a material with cubic symmetry.

Further non-limiting description of various aspects of the invention are provided in 1) an article published in Chemical Science, Vol. 3, pg 2429 on May 24, 2012 along with its supplemental information, 2) an article published in Chem-Comm Vol. 48, pages 9828-9830 on Aug. 29, 2012, along with its supplemental information, and 3) a manuscript published in January 2013 along with its supplemental information in *Chem. Commun.*, 2013, 49, 1419-1421, all of which are incorporated herein by reference.

1 (a) S. Ma and H. C. Zhou, *Chem. Comm.*, 2010, 46, 44; (b) M. P. Suh, H. J. Park, T. K. Prasad and D. W. Lim, *Chem. Rev.*, 2012, 112, 782.

2 J. R. Li, J. Sculley and H. C. Zhou, *Chem. Rev.*, 2012, 112, 869.

3 K. Sumida, D. L. Rogow, J. A. Mason, T. M. McDonald, E. D. Bloch, Z. R. Herm, Y. S. Bae and J. R. Long, *Chem. Rev.*, 2012, 112, 724.

4 M. Yoon, R. Srirambalaji and K. Kim, *Chem. Rev.,* 2012, 112, 1196.

5 (a) K. Koh, A. G. Wong-Foy and A. J. Matzger, *J. Am. Chem. Soc.,* 2009, 131, 4184; (b) H. Furukawa, N. Ko, Y. B. Go, N. Aratani, S. B. Choi, E. Choi, A. O. Yazaydin, R. Q. Snurr, M. O'Keeffe, J. Kim and O. M. Yaghi, *Science,* 2010, 329, 424; (c) K. Koh, J. D. V. Oosterhout, S. Roy, A. G. Wong-Foy and A. J. Matzger, *Chem. Sci.,* 2012, 3, 2429.

6 (a) K. K. Tanabe, Z. Wang and S. M. Cohen, *J. Am. Chem. Soc.,* 2008, 130, 8508; (b) Z. Wang and S. M. Cohen, *J. Am. Chem. Soc.,* 2007, 129, 12368; (c) Z. Wang, S. M. Cohen, *Angew. Chem., Int. Ed.,* 2008, 47, 4699.

7 (a) A. P. Nelson, 0. K. Farha, K. L. Mulfort and J. T. Hupp, *J. Am. Chem. Soc.,* 2009, 131, 458; (b) O. K. Farha, A. O. Yazaydin, I. Eryazici, C. D. Malliakas, B. G. Hauser, M. G. Kanatzidis, S. T. Nguyen, R. Q. Snurr and J. T. Hupp, *Nat. Chem.,* 2010, 2, 944; (c) J. An, 0. K. Farha, J. T. Hupp, E. Pohl, J. I. Yeh and N. L. Rosi, *Nat. Commun.,* 2012, 3, 604; (d) Z. H. Xiang, D. P. Cao, X. H. Shao, W. C. Wang, J. W. Zhang and W. Z. Wu, *Chem. Eng. Sci.,* 2010, 65, 3140; (e) S. T. Meek, J. J. Perry, L. T. M. Stephanie, J. A. Greathouse and M. D. Allendorf, *Cryst. Growth Des.,* 2011, 11, 4309; (f) K. Gedrich, I. Senkovska and N. Klein, *Angew. Chem. Int. Ed.,* 2010, 49, 8489; (g) D. Han, F. L. Jiang, M. Y. Wu, L. Chen, Q. H. Chen and M. C. Hong, *Chem. Commun.,* 2011, 47, 9861.

8 (a) H. K. Chae, D. Y. Siberio-Perez, J. Kim, Y-B. Go, M. Eddaoudi, A. J. Matzger, M. O'Keeffe, O. M. Yaghi, *Nature,* 2004, 427, 523; (b) H. Furukawa, M. A. Miller and O. M. Yaghi, *J. Mater. Chem.,* 2007, 17, 3197; (c) A. G. Wong-Foy, A. J. Matzger and O. M. Yaghi, *J. Am. Chem. Soc.,* 2006, 128, 3494; (d) Z. R. Herm, J. A. Swisher, B. Smit, R. Krishna and J. R. Long, *J. Am. Chem. Soc.,* 2011, 133, 5664.

9 (a) S. S. Kaye, A. Dailly, O. M. Yaghi and J. R. Long, *J. Am. Chem. Soc.,* 2007, 129, 14176; (b) J. L. C. Rowsell, A. R. Millward, K. S. Park and O. M. Yaghi, *J. Am. Chem. Soc.,* 2004, 126, 5666.

10 (a) J. H. Cavka, S. Jakobsen, U. Olsbye, N. Guillou, C. Lamberti, S. Bordiga and K. P. Lillerud, *J. Am. Chem. Soc.,* 2008, 130, 13850; (b) Q. Y. Yang and A. D. Wiersum, *J. Phys. Chem. C,* 2011, 115, 13768; (c) S. Chavan, J. G. Vitillo, M. J. Uddin, F. Bonino, C. Lamberti, E. Groppo, K. P. Lillerud and S. Bordiga, *Chem. Mater.,* 2010, 22, 4602; (d) P. S. Barcia, D. Guimaraes, P. A. P. Mendes, J. A. C. Silva, V. Guillerm, H. Chevreau, C. Serre and A. E. Rodrigues, *Micropor. Mesopor. Mater.,* 2011, 139, 67; (e) K. Mathivathani, M. H. Nilsen, S. Usseglio, S. Jakobsen, U. Olsbye, M. Tilset, C. Larabi, E. A. Quadrelli, F. Bonino and K. P. Lillerud, *Chem. Mater.,* 2010, 22, 6632; (f) L. Valenzano, B. Civalleri, S. Chavant, S. Bordigat, M. H. Nilsen, S. Jakobsen, K. P. Lillerud and C. Lamberti, *Chem. Mater.,* 2011, 23, 1700.

11 (a) J. L. C. Rowsell and O. M. Yaghi, *J. Am. Chem. Soc.,* 2006, 128, 1304; (b) A. C. Kizzie, A. G. Wong-Foy and A. J. Matzger, *Langmuir,* 2011, 27, 6368; (c) J. A. Botasa, G. Callejaa, M. Sanchez-Sanchez and M. G. Orcajoa, *Int. J. Hydrogen Energy,* 2011, 36, 10834; (d) Y. Liu, H. Kabbour, C. M. Brown, D. A. Neumann and C. C. Ahn, *Langmuir* 2008, 24, 4772; (e) H. Wu, W. Zhou and T. Yildirim, *J. Am. Chem. Soc.,* 2009, 131, 4995.

12 (a) S. S. Y. Chui, S. M. F. Lo, J. P. H. Charmant, A. G. Orpen and I. D. Williams, *Science,* 1999, 283, 1148; (b) A. O. Yazaydin, A. I. Benin, S. A. Faheem, P. Jakubczak, J. J. Low, R. R. Willis and R. Q. Snurr, *Chem. Mater.,* 2009, 21, 1425.

13 (a) A. G. Wong-Foy, O. Lebel and A. J. Matzger, *J. Am. Chem. Soc.,* 2007, 129, 15740; (b) C. S. Lim, J. K. Schnobrich, A. G. Wong-Foy and A. J. Matzger, *Inorg. Chem.,* 2010, 49, 5271; (c) K. A. Cychosz, A. G. Wong-Foy and A. J. Matzger, *J. Am. Chem. Soc.,* 2008, 130, 6938; (d) K. A. Cychosz, A. G. Wong-Foy and A. J. Matzger, *J. Am. Chem. Soc.,* 2009, 131, 14538; (e) T. H. Park, K. A. Cychosz, A. G. Wong-Foy, A. Dailly and A. J. Matzger, *Chem. Commun.* 2011, 47, 1452.

We claim:

1. A method for treating a solvent-containing metal organic framework material (MOF) to increase its internal surface area or porosity, comprising introducing a composition consisting of $CO_2$ into a vessel containing the solvent-containing MOF, while venting the $CO_2$ and maintaining supercritical conditions for carbon dioxide in the vessel.

2. The method of claim 1 wherein the solvent is not miscible in supercritical $CO_2$.

3. The method of claim 1 where the solvent is the solvent of synthesis of the MOF.

4. The method of claim 3, wherein the solvent is selected from the group consisting of diethylformamide and dimethylformamide.

5. The method of claim 3 wherein the material is treated directly after synthesis without exchanging the solvent of synthesis.

6. The method of claim 1 comprising venting the $CO_2$ while maintaining sufficient pressure for liquid $CO_2$ to be present in the vessel.

7. The method of claim 1 wherein introducing $CO_2$ into the vessel comprises adding gaseous $CO_2$ at a pressure at which it forms liquid $CO_2$, continuing to add $CO_2$ until the vessel is full of liquid $CO_2$, and then raising the temperature and/or pressure to achieve supercritical conditions for $CO_2$.

8. The method of claim 1 further comprising venting the $CO_2$ while maintaining conditions for liquid $CO_2$ in the vessel.

9. A method according to claim 1, wherein the MOF material is made by reacting a metal cation with an organic linker selected from:

9,10-Anthracenedicarboxylic acid,

Biphenyl-3,3',5,5'-tetracarboxylic acid

-continued

Biphenyl-3,4′,5-tricarboxylic acid 2,2′-Diamino-4,4′-stilbenedicarboxylic acid

5-Cyano-1,3-benzenedicarboxylic acid, 2,5-Diaminoterephthalic acid     2,5-Dihydroxyterephthalic acid 2,2′-Dinitro-4,4′-stilbenedicarboxylic acid 2-Hydroxyterephthalic acid     malonic acid 2,6-Naphthalenedicarboxylic acid terephthalic acid

[1,1′:4′,1″]Terphenyl-3,3″,5,5″-tetracarboxylic acid 3,3′,5,5′-Tetracarboxydiphenylmethane 1,2,4,5-Tetrakis(4-carboxyphenyl)benzene 4,4',4''-s-Triazine-2,4,6-triyl-tribenzoic acid trimesic acid, or benzene-1,3,5-tricarboxylic acid,

1,3,5-Tris(4'-carboxy[1,1'-biphenyl]-4-yl)benzene

1,3,5-Tris(4-carboxyphenyl)benzene ethanedioic acid,    propanedioic acid = malonic acid, butanedioic acid      pentanedioic acid citric acid      phthalic acid isophthalic acid 4,4',4''-[benzene-1,3,5-triyl-tris(ethyne-2,1-diyl)]tribenzoate (BTE), biphenyl-4,4'-dicarboxylate (BPDC), benzene-1,3,5-tris(1H-tetrazole) (BTT), 4,4'-bipyridine, 2-Methylimidazole, and Imidazole.

10. A method according to claim 9, wherein the metal is selected from $Zn^{2+}$, $Cu^{2+}$, $Mg^{2+}$, $Ni^{2+}$, $Co^{2+}$, and $Mn^{2+}$.

11. A method of making a porous material, comprising:
   a) combining a metal salt and an organic linker in a solvent or solvents of reaction in which both are soluble,
   b) exposing the combined metal salt and organic linker to conditions under which they react to form a porous material comprising a metal-organic framework,
   c) obtaining crystals of the porous material from the reaction mixture of step b), wherein the crystals comprise the metal-organic framework material and occluded solvent of reaction, and
   d) exposing the crystals to a composition consisting of flowing supercritical carbon dioxide to remove occluded solvent from the crystals and provide an activated material.

12. A method according to claim 11, wherein the linker comprises two or more carboxyl groups attached to an aromatic ring of the linker.

13. A method according to claim 11, wherein the linker comprises two or more nitrogen-containing aromatic rings.

14. A method according to claim 11, wherein the occluded solvent is not miscible in supercritical carbon dioxide.

15. A method according to claim 11, further comprising exchanging the reaction solvent with a second solvent before exposing the material to flowing supercritical carbon dioxide.

16. A method according to claim 11, wherein the solvent or solvents of reaction are not exchanged with another solvent prior to exposure to flowing supercritical carbon dioxide.

17. A method according to claim 11, wherein the metal salt comprises a salt of $Zn^{2+}$, $Cu^{2+}$, $Mn^{2+}$, or $Mg^{2+}$.

18. A method according to claim 11, wherein the linker is selected from the group consisting of

9,10-Anthracenedicarboxylic acid,

Biphenyl-3,3′,5,5′-tetracarboxylic acid

Biphenyl-3,4′,5-tricarboxylic acid

2,2′-Diamino-4,4′-stilbenedicarboxylic acid

5-Cyano-1,3-benzenedicarboxylic acid,

2,5-Diaminoterephthalic acid    2,5-Dihydroxyterephthalic acid

2,2′-Dinitro-4,4′-stilbenedicarboxylic acid

2-Hydroxyterephthalic acid    malonic acid

2,6-Naphthalenedicarboxylic acid terephthalic acid

[1,1′:4′,1″]Terphenyl-3,3″,5,5″-tetracarboxylic acid

3,3′,5,5′-Tetracarboxydiphenylmethane

1,2,4,5-Tetrakis(4-carboxyphenyl)benzene

4,4',4''-s-Triazine-2,4,6-triyl-tribenzoic acid trimesic acid, or benzene-1,3,5-tricarboxylic acid, 1,3,5-Tris(4'-carboxy[1,1'-biphenyl]-4-yl)benzene 1,3,5-Tris(4-carboxyphenyl)benzene ethanedioic acid, propanedioic acid = malonic acid, butanedioic acid, pentanedioic acid citric acid, phthalic acid isophthalic acid 4,4',4''-[benzene-1,3,5-triyl-tris(ethyne-2,1-diyl)]tribenzoate (BTE),
biphenyl-4,4'-dicarboxylate (BPDC),
benzene-1,3,5-tris(1H-tetrazole) (BTT),
4,4'-bipyridine,
2-Methylimidazole, and
Imidazole.

19. A method of making and activating a porous material comprising a metal organic framework (MOF), comprising reacting a metal cation selected from $Zn^{2+}$, $Cu^{2+}$, $Mg^{2+}$, $Ni^{2+}$, $Co^{2+}$, $Mn^{2+}$ with an organic linker composition in a solvent to form a MOF material having occluded solvent of synthesis,
optionally exposing the MOF material to a second solvent to exchange out the solvent of synthesis, and
drying the MOF material by exposing the MOF material containing either the solvent of synthesis or the second solvent to conditions of flowing supercritical carbon dioxide to make the activated porous material.

20. A method for the treatment of a solvent-containing metal organic framework material (MOF) to increase its internal surface area or porosity, comprising introducing $CO_2$ into a vessel containing the solvent-containing MOF, and venting the $CO_2$ while maintaining conditions for liquid carbon dioxide in the vessel.

* * * * *